US00PP20496P2

(12) United States Plant Patent
Glick

(10) Patent No.: US PP20,496 P2
(45) Date of Patent: Nov. 17, 2009

(54) ***EUPHORBIA* PLANT NAMED 'AUTUMN SUNSET'**

(50) Latin Name: *Euphorbia griffithii*
Varietal Denomination: Autumn Sunset

(76) Inventor: Barry Glick, HC 67 PO 539B, Renick, WV (US) 24966

( * ) Notice: Subject to any disclaimer, the term of this patent is extended or adjusted under 35 U.S.C. 154(b) by 0 days.

(21) Appl. No.: 12/157,177

(22) Filed: Jun. 6, 2008

(51) Int. Cl.
*A01H 5/00* (2006.01)

(52) U.S. Cl. ..... Plt./302

(58) Field of Classification Search ..... Plt./302
See application file for complete search history.

*Primary Examiner*—Annette H Para

(57) ABSTRACT

A new and distinct *Euphorbia griffithii×ephithymoides* cultivar named 'AUTUMN SUNSET' is disclosed, characterized by distinct bright orange floral bracts, upright plant shape and free flowering habit. The new variety is a *Euphorbia* hybrid, and naturally blooms during June and July.

1 Drawing Sheet

Figure 1:
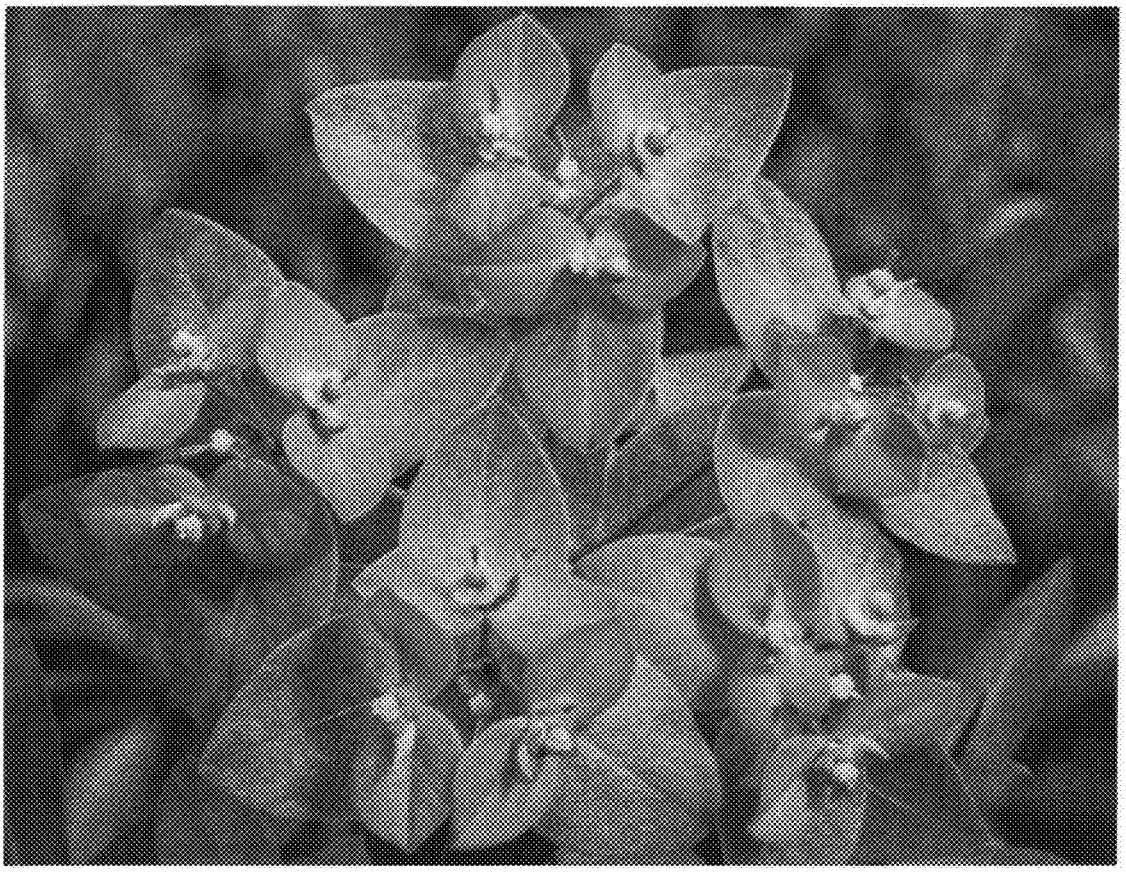

Latin name of the genus and species: *Euphorbia griffithii.* Variety denomination: 'AUTUMN SUNSET'.

BACKGROUND OF THE INVENTION

The new cultivar is the product of a planned breeding program under the direction of the inventor, Barry Glick, a citizen of the United States. The objective of the breeding program was to produce *Euphorbia* cultivars with unique flower colors. The seed parent is the unpatented, variety referred to as *Euphorbia griffithii* 'Fireglow.' The pollen parent is *Euphorbia ephithymoides*, unpatented. The new variety was discovered June 1998, by the inventor in a group of seedlings resulting from that crossing, in Renick, W. Va.

Asexual reproduction of the new cultivar 'AUTUMN SUNSET' by vegetative cuttings was performed in Renick, W. Va. and has shown that the unique features of this cultivar are stable and reproduced true to type in successive generations.

SUMMARY OF THE INVENTION

The cultivar 'AUTUMN SUNSET' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'AUTUMN SUNSET' These characteristics in combination distinguish 'AUTUMN SUNSET' as a new and distinct *Euphorbia* cultivar:

1. Free flowering habit.
2. Distinctive solid bright orange floral structures.
3. Upright plant shape.

PARENT COMPARISON

Plants of the new cultivar 'AUTUMN SUNSET' are similar to plants of the seed parent, *Euphorbia griffithii* 'Fireglow' in most horticultural characteristics, however, plants of the new cultivar 'AUTUMN SUNSET' produce floral bracts of a solid orange color, compared to reddish/orange. Plants of the new variety are more upright than the seed parent. Additionally, plants of the new variety have green stems, peduncles and pedicels, compared to the red stems, peduncles and pedicels of 'Fireglow.'

Plants of the new cultivar 'AUTUMN SUNSET' are similar to plants of the pollen parent, *Euphorbia epithymoides* in most horticultural characteristics, however, plants of the new cultivar 'AUTUMN SUNSET' are taller and have narrower leaves. Additionally floral bracts of 'AUTUMN SUNSET' are orange, compared to the pollen parent yellowish green floral bracts.

The parent varieties represent the best commercial comparisons.

BRIEF DESCRIPTION OF THE PHOTOGRAPH

The accompanying photograph in FIG. 1 illustrates in full color a close-up of typical floral bracts and leaves of 'AUTUMN SUNSET' grown outdoors old. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart except where general terms of ordinary dictionary significance are used. The following observations and measurements describe 'AUTUMN SUNSET' plants grown in a commercial greenhouse in Renick, W. Va. during June and July. The growing temperature ranged from approximately 9 to 14° C. at night to 21 to 29° C. during the day. Measurements and numerical values represent averages of typical flowering types. No chemical or photoperiodic treatments were given.

Botanical classification: *Euphorbia griffithii×epithymoides* cultivar 'AUTUMN SUNSET.'

PROPAGATION

Time to rooting: 10 to 14 days at approximately 21° C.
Root description: Thick, well branched.

PLANT

Growth habit: Upright, columnar, perennial subshrub.
Height: Approximately 105 cm.
Plant spread: Approximately 60 cm.
Age of plant described: Approximately 2 years.
Growth rate: Moderate.
Branching characteristics: Moderate branching.
Length of lateral branches: Approximately 20 cm.
Diameter of lateral branches: Approximately 0.5 cm.
Texture of lateral branches: Smooth, pubescence at nodes.
Internode length: Approximately 2 cm.
Strength of stem: Flexible and strong.
Color of lateral branches: Near RHS Green 144A.
Aspect: Upright.
Number of leaves per lateral branch: Approximately 20.

FOLIAGE

Leaf: Two types, Basal, on plant stems, whorled, near inflorescence Basal Leaves:
- *Arrangement.*—Alternate, single.
- *Average length.*—Approximately 14.0 cm.
- *Average width.*—Approximately 3.8 cm.
- *Shape of blade.*—Oblanceolate.
- *Apex.*—Acute.
- *Base.*—Cordate.
- *Attachment.*—Sessile.
- *Margin.*—Entire.
- *Texture of top surface.*—Smooth, leathery.
- *Texture of bottom surface.*—Smooth.
- *Leaf internode length.*—Approximately 0.7 cm.
- *Color.*—Young foliage upper side: Near R.H.S. Yellow-Green 144A. Young foliage under side: Near RHS Yellow-Green147C. Mature foliage upper side: Near RHS Yellow-Green 147A. Mature foliage under side: Near RHS Yellow-Green 147B.
- *Venation.*—Type: Pinnate. Venation color upper side: Near RHS Yellow-Green 147D. Venation color under side: Near RHS Yellow-Green 146B.

Petiole: Not present.
Whorl leaves:
- *Arrangement.*—Avg. 5 in a whorl at the base of primary cymes; Avg. 3 at the base of secondary cymes.
- *Average length.*—Approximately 5 cm.
- *Average width.*—Approximately 2 cm.
- *Shape of blade.*—Oblanceolate.
- *Apex.*—Acute.
- *Base.*—Cordate.
- *Attachment.*—Sessile.
- *Margin.*—Entire.
- *Texture of top surface.*—Smooth, leathery.
- *Texture of bottom surface.*—Smooth.
- *Color.*—Young foliage upper side: Near R.H.S. Yellow-Green 144A with Yellow 13A. Young foliage under side: Near RHS Yellow 13A with Yellow-Green146B. Mature foliage upper side: Primarily near RHS Orange N25A, with Orange 25B and Yellow 15B. Slight Yellow-Green 144A near tip. Mature foliage under side: Primarily near RHS Orange 25B and Yellow 15B. Slight Yellow-Green 144A near tip.
- *Venation.*—Type: Pinnate. Venation color upper side: Near RHS Yellow 8B. Venation color under side: Near RHS Yellow13C.

FLOWER

Bloom period: Naturally blooming late June through mid July in W. Va.
Bud:
- *Bud shape.*—Spherical.
- *Bud length.*—Approximately 0.05 cm.
- *Bud diameter.*—Approximately 0.05 cm.
- *Bud color: Between Yellow-Green* 145A and 145B.

Inflorescence:
- *Form.*—Umbel-like compound cyme. Primary Cymes: 5-merous. Secondary Cymes: 3-merous.
- *Measurement of average primary cyme.*—Diameter of entire inflorescence: Approximately 8 cm. Depth of entire inflorescence: Approximately 5 cm.

Individual flowers:
- *Length.*—Approximately 2 cm.
- *Width.*—Approximately 0.9 cm.
- *Aspect.*—Upright.
- *Duration on plant.*—Approximately 3 to 4 weeks. Persistent.

Fragrance: None.
Floral bracts:
- *Arrangement.*—2 or 3 opposite or whorled, subtending cyathium.
- *Shape.*—Broadly ovate.
- *Apex.*—Acute.
- *Base.*—Attenuate.
- *Length.*—0.8 cm, average.
- *Width.*—0.7 cm.
- *Texture.*—Glaborous.
- *Color.*—Upper side of immature bract: Edge Near RHS Orange-Red N30A/B. Mid-bract: Near R.H.S. Orange-Red 30B. Interior-bract: Near RHS Yellow 13A. Under side of immature bract: Edge Near RHS Orange-Red N30A. Mid-bract: Near R.H.S. Orange-Red 30B. Interior-bract: Near RHS Yellow 13A. Upper side of mature bract: Edge with slight coloration Near RHS Orange-Red N30A/B. Mid-bract: Near RHS Orange 28B and Orange 25A. Interior-bract: Near RHS Yellow 13A. Under side of mature bract: Near RHS Orange-Red N30A/B. Mid-bract: Near RHS Orange 28B and Orange 25A. Interior-bract: Near RHS Yellow 13A.

Cyathia:
- *Arrangement.*—Involucre of cyathium cup-shaped;4-lipped, upright.
- *Other.*—3 petaloid appendages subtending the cyathia: Height: Approx. 0.3 cm. Diameter: Approx. 0.5 cm. Color Immature: Near RHS Yellow 12A. Color Mature: Near RHS Orange 25B.

Peduncle:
- *Peduncle length.*—Approximately 2.3.
- *Peduncle diameter.*—Approximately 1 cm.
- *Angle.*—Approximately 45 deg from center of whorl.
- *Color.*—Near RHS Orange 26B 144A.

Pedicils:
- *Length.*—Approx. 0.5 cm.
- *Diameter.*—Approx. 0.1 cm.

*Angle.*—Near 45 deg. from vertical.
*Strength.*—Strong, flexible.
*Texture.*—Smooth.
*Color.*—Near RHS Yellow-Green 152C.

REPRODUCTIVE ORGANS

*Androecium.*—Stamens: 2 to 4, branched and holding 4 anthers. Anther shape: Bi-lobed. Anther length: Approximately 0.05 cm. Anther color: Near RHS 22AFilament colored red 51A. Pollen quantity: None observed.

*Gynoecium.*—Pistil number: 1. Pistil shape: Tri-parted. Pistil length: Approx. 0.5 cm. Style length: Approx. 0.2 cm. Style color: Near RHS 154B. Stigma shape: Bi-lobed. Stigma color: Near RHS Orange-Red 33A. Ovary diameter: Near RHS 0.2 cm. Ovary color: Near RHS 1 54A.

OTHER CHARACTERISTICS

Disease resistance: Neither resistance nor susceptibility to diseases or pests has been observed in this variety.

Drought tolerance and cold tolerance: Tender perennial. Tolerates high temperature to at least 32° C. Tolerates low temperatures to −32° C. Drought tolerance has not been observed.

Fruit/seed production: Fruit and seed production not observed.

What is claimed is:

1. A new and distinct cultivar of *Euphorbia* plant named 'AUTUMN SUNSET' as herein illustrated and described.

* * * * *